(12) United States Patent
Lang et al.

(10) Patent No.: US 12,145,897 B2
(45) Date of Patent: Nov. 19, 2024

(54) PREPARATION OF CHIRAL PRIMARY AMINE FROM ASYMMETRIC REDUCTIVE AMINATION OF SIMPLE KETONE CATALYZED BY RUTHENIUM-DIPHOSPHINE CATALYST

(71) Applicants: SHENZHEN CATALYS TECHNOLOGY CO., LTD, Guangdong (CN); Shenzhen Innovation Center of Small Molecule Drug Discovery Co., Ltd., Guangdong (CN)

(72) Inventors: Qiwei Lang, Guangdong (CN); Xiaobing Ding, Guangdong (CN); Shaobai Yan, Guangdong (CN)

(73) Assignees: SHENZHEN CATALYS TECHNOLOGY CO., LTD, Shenzhen (CN); Shenzhen Innovation Center of Small Molecule Drug Discovery Co., Ltd., Shenzhen (CN)

( * ) Notice: Subject to any disclaimer, the term of this patent is extended or adjusted under 35 U.S.C. 154(b) by 622 days.

(21) Appl. No.: 17/389,633

(22) Filed: Jul. 30, 2021

(65) Prior Publication Data
US 2022/0017451 A1  Jan. 20, 2022

Related U.S. Application Data

(63) Continuation of application No. PCT/CN2019/122355, filed on Dec. 2, 2019.

(30) Foreign Application Priority Data

Jan. 30, 2019 (CN) .......................... 201910092496.2

(51) Int. Cl.
  *C07C 209/26* (2006.01)
  *C07C 213/02* (2006.01)
  *C07C 269/06* (2006.01)

(52) U.S. Cl.
  CPC .......... *C07C 209/26* (2013.01); *C07C 213/02* (2013.01); *C07C 269/06* (2013.01); *C07C 2602/10* (2017.05); *C07C 2602/12* (2017.05)

(58) Field of Classification Search
  CPC ... C07C 209/26; C07C 213/02; C07C 211/27; C07C 217/58
  See application file for complete search history.

(56) References Cited

U.S. PATENT DOCUMENTS 8,431,741 B2 * 4/2013 Veghini ................ C07C 227/32
562/567

FOREIGN PATENT DOCUMENTS

WO  2005028419 A  3/2005

OTHER PUBLICATIONS

Tan, X., et al., Asymmetric synthesis of chiral primary amines by ruthenium-catalyzed direct reductive amination of alkyl aryl ketones with ammonium salts and molecular H2, Journal of the American Chemical society, 140(6), Jan. 29, 2018, pp. 2024-2027 (Year: 2018).*

(Continued)

*Primary Examiner* — Yate' K Cutliff

(57) ABSTRACT

The present invention relates to a preparation method of chiral primary amine. The chiral primary amine is prepared through a one-pot method that under the action of a ruthenium-chiral diphosphine catalyst, a simple ketone and an ammonium salt $RCOONH_4$ have reductive amination by adding hydrogen and then are heated and hydrolyzed by adding acid. The present invention has the advantages of good substrate universality, high reaction efficiency and the like

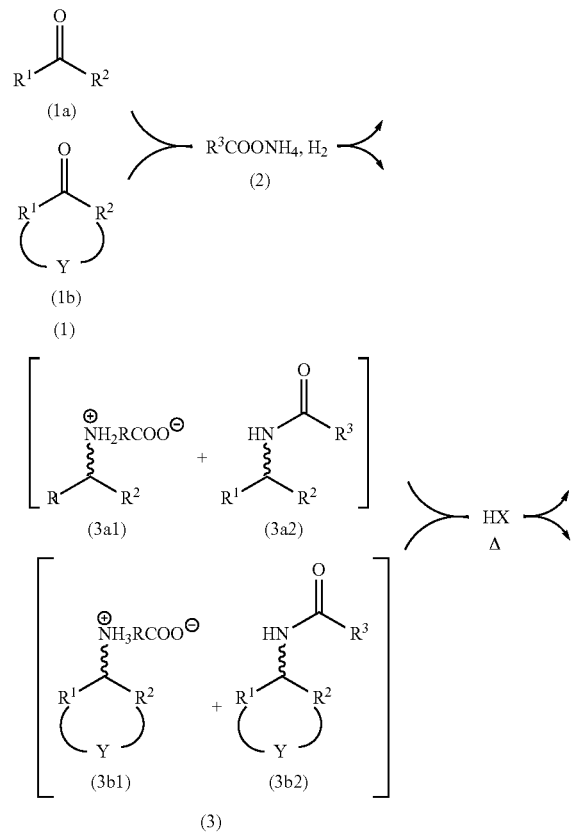

(Continued)

-continued

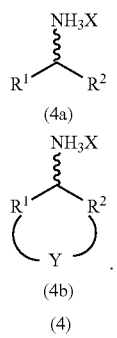

6 Claims, No Drawings

(56) References Cited

OTHER PUBLICATIONS

Tan, X., et al., Asymmetric synthesis of chiral primary amines by ruthenium-catalyzed direct reductive amination of alkyl aryl ketones with ammonium salts and molecular H2, Journal of the American Chemical society, 140(6), Jan. 29, 2018, Supporting Information, pp. S1-S74 (Year: 2018).*

Li, W., et al., Hithly efficient and highly enantioselective asymmetric hydrogenation of ketones with TunesPhos/1,2-Diamine-Ruthenium(II) complexes, J. Org. Chem., vol. 74, No. 3, pp. 1397-1399 (Year: 2009).*

Sun, X., et al., synthesis of C3*-TunePhos Chiral ligands and their application in hydrogenation, Synfacts, Georg Thime Verlag Stuttgarg, (2), pp. 0194-0194 (Year: 2010).*

Joan,G D.et al."Direct Asymmetric Ruthenium-Catalyzed Reductive Amination of Alkyl-Aryl Ketones with Ammonia and Hydrogen." Journal of the American Chemical Society.,vol. 140,No. 1,Dec. 1, 2017, ISSN:0002-7863, pp. 355-361.

Lou,Yazhou et al."Dynamic Kinetic Asymmetric Reductive Amination: Synthesis Of Chiral Primary β-Amino Lactams." Angewandte Chemie, International Edition., vol. 57,No. 43,Oct. 2, 2018, ISSN: 1433-7851, pp. 14193-14197.

Xuefeng Tan. "Asymmetric Synthesis of Chiral Primary Amines by Ruthenium-Catalyzed Direct Reductive Amination of Alkyl Aryl Ketones with Ammonium Salts and Molecular H2." J. Am. Chem. Soc.,vol. 140,Jan. 29, 2018, pp. 2024-2027.

Anja K. Holze et al."Asymmetric Biocatalytic Amination of Ketones at the Expense of NH3 and Molecular Hydrogen." Org. Lett. vol. 17,pp. 24311-2433.

* cited by examiner

PREPARATION OF CHIRAL PRIMARY AMINE FROM ASYMMETRIC REDUCTIVE AMINATION OF SIMPLE KETONE CATALYZED BY RUTHENIUM-DIPHOSPHINE CATALYST

TECHNICAL FIELD

The present invention relates to a preparation method of chiral primary amine with a simple ketone and an ammonium salt as raw materials, in particular to preparation of the chiral primary amine through asymmetric reductive amination of the simple ketone catalyzed by a ruthenium-diphosphine catalyst.

BACKGROUND OF THE PRESENT INVENTION

Chiral amine structures widely exist in organisms in the nature and are applied to synthesis of chiral drugs and total synthesis of natural products. The synthesis of chiral amine is achieved by converting chiral alcohols or chiral halogenated substances. The chiral alcohols and the chiral halogenated substances are not easy to be obtained, while ketone compounds are very easy to be obtained. Methods for preparing the chiral amine through a ketone include a direct method and an indirect method. In the indirect method, the ketone firstly reacts with amine to prepare imine and then the chiral amine is obtained through asymmetric hydrogenation. In the other method, the ketone and amine generate imine in situ and the imine is subjected to asymmetric hydrogenation to obtain the chiral amine, namely asymmetric reductive amination. Reductive amination has the advantage that there is no need of separating out imine intermediates sensitive to water, and has the challenge of selectively reducing imine while not reducing a ketone.

Japan Takasago Company's patent in 2005 protected asymmetric reductive amination of β-ketone ester[1]. With ammonium acetate as an ammonium source and hydrogen as a reducing agent, β-chiral amino acid derivatives are obtained with high enantioselectivity and yield. Most reductive amination using hydrogen as a hydrogen source reported later is based on ligand modification and substrates with special functional groups, such as application of ClMeOBIPHEP[2] and SegPhos[3], as well as on synthesis of useful medicine intermediates, such as Sitagliptin[4] and (S)-3-amino-4-methoxyl-1-butanol[5].

In addition, the following technical solution[6] is obtained in early study of the applicant:

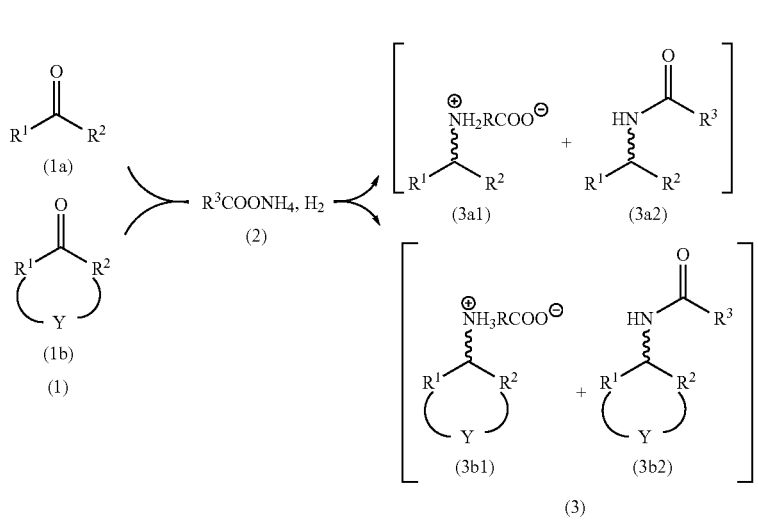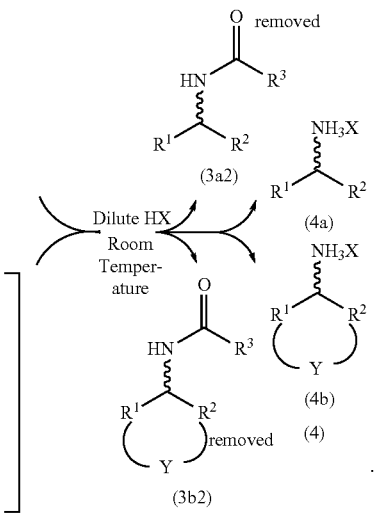

In the technical solution, when chiral primary amine is prepared, according to technical knowledge mastered by the applicant, it is considered that no other intermediate that can be converted into a target product exists, so that substances, except (3a1) and (3b1), are all separated and removed as impurities. The present invention is improved based on the aforementioned process, and it is accidentally found that the reaction yield is further increased by adding acid HX in reaction to hydrolyze amide to obtain a product and by adopting one-pot method for preparation. By further researching the reason, it is found that the reason is generation of intermediate products such as (3a2) and (3b2).

[1] Matsumura, K.; Saito, T. PCT Patent Appl. WO 2005/028419A3, 2005
[2] Bunlaksananusorn, T.; Rampf, F. Synlett 2005, 2682-2684
[3] Shimizu, H.; Nagasaki, I.; Matsumura, K.; Sayo, N.; Saito, T. Acc. Chem. Res. 2007, 40, 1385-1393
[4] Steinhuebel, D.; Sun, Y.; Matsumura, K.; Sayo, N.; Saito, T. J. Am. Chem. Soc. 2009, 131, 11316-11317
[5] Mattei, P.; Moine, G.; Püntener, K.; Schmid, R. Org. Process Res. Dev. 2011, 15, 353-359
[6] Xuefeng Tan, et al, J. Am. Chem. Soc. 2018, 140, 2024-2027

SUMMARY OF THE PRESENT INVENTION

The technical problem to be solved by the present invention is to obtain chiral primary amine through reductive amination of a simple ketone. The chiral primary amine is synthesized through a one-pot method under the action of acid with the simple ketone and an ammonium salt as raw materials and with a ruthenium-diphosphine complex as a catalyst.

In the prior art, generated amide products are ignored in a post-treatment process and are directly extracted with an organic solvent and thrown away. The present invention finds that some acylated products will be generated in a reaction system. After adding acid in post-treatment, the amide products can be converted into amine products by heating and hydrolysis, so that the yield is higher.

According to a preparation method of chiral primary amine provided by the present invention, as shown in the following formula, a simple ketone (1) is converted into an intermediate (3) under the action of an ammonium salt (2), hydrogen and a catalyst, and then an amine salt (4) is generated by heating and hydrolysis after acid HX is added.

phosphate radical, the monohydrogen phosphate radical, the phosphite radical, the nitrate radical, etc. L is a chiral diphosphine ligand, as shown in formula (6):

In above formula (6), linker represents various chiral and achiral linking groups. $R^3$ to $R^6$ represent identical or different substituent groups, including alkyl, cycloalkyl, aryl, aralkyl, alkoxy, cycloalkoxy, aryloxy, aralkoxy and heterocyclyl. A ring is formed between $R^1$ and $R^2$. In addition, the

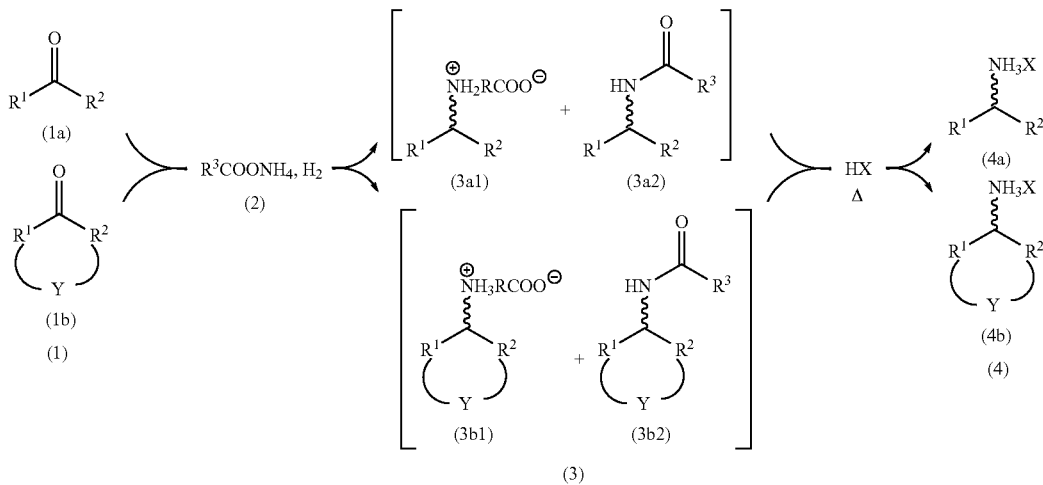

The above formula (1) represents the simple ketone, and $R^1$ and $R^2$ represent different substituent groups, including alkyl, cycloalkyl, aryl, aralkyl, alkoxy, cycloalkoxy, aryloxy, aralkoxy and heterocyclyl. In addition, the alkyl, the cycloalkyl, the aryl, the aralkyl, the alkoxy, the cycloalkoxy, the aryloxy, the aralkoxy and the heterocyclyl also have substituent groups. Y represents different linking groups linking $R^1$ and $R^2$ into different cyclic ketones.

The above formula (2) represents a carboxylic acid ammonium salt. $R^3$ represents different substituent groups, including alkyl, cycloalkyl, aryl, aralkyl, alkoxy, cycloalkoxy, aryloxy, aralkoxy and heterocyclyl. In addition, the alkyl, the cycloalkyl, the aryl, the aralkyl, the alkoxy, the cycloalkoxy, the aryloxy, the aralkoxy and the heterocyclyl also have substituent groups.

$H_2$ in the above formula represents hydrogen.

HX in the above formula represents protonic acid, and X is halogen anions, carboxylate anions, sulfooxy anions, a sulfate radical, a hydrogen sulfate radical, a dihydrogen phosphate radical, a monohydrogen phosphate radical, a phosphite radical, a nitrate radical, etc.

The catalyst used for the reductive amination in the above reaction formula is as shown in formula (5):

$$RuX_2L \quad (5)$$

In formula (5), Ru represents metallic ruthenium.

X in formula (5) is a complex anion, and is the halogen anions, the carboxylate anions, the sulfooxy anions, the sulfate radical, the hydrogen sulfate radical, the dihydrogen alkyl, the cycloalkyl, the aryl, the aralkyl, the alkoxy, the cycloalkoxy, the aryloxy, the aralkoxy and the heterocyclyl also have substituent groups.

The reducing agent required for the above reductive amination is $H_2$, and pressure is 10 to 100 atm. A required reaction solvent is methanol, ethanol, isopropanol, butanol, tert-butanol, difluoroethanol, trifluoroethanol, hexafluoroisopropanol, tetrahydrofuran, toluene, dichloromethane, and 1,2-dichloroethane. A reaction temperature is 20° C. to 150° C., and reaction time is 0.5 to 240 h. In post-treatment, acid is used for heating first, and corresponding chiral amine is obtained through simple extraction and neutralization operations and the like.

As a preferred technical solution of the present invention, above formula (1) represents the simple ketone, and $R^1$ and $R^2$ represent different substituent groups, including alkyl, cycloalkyl, aryl, aralkyl, alkoxy, cycloalkoxy, aryloxy, aralkoxy and heterocyclyl. In addition, the alkyl, the cycloalkyl, the aryl, the aralkyl, the alkoxy, the cycloalkoxy, the aryloxy, the aralkoxy and the heterocyclyl also have substituent groups. Y represents different linking groups linking $R^1$ and $R^2$ into different cyclic ketones.

Description of $R^1$ and $R^2$ in formula (1) As a preferred technical solution of the present invention, as the alkyl, linear or branched alkyl with a carbon number of 1 to 50, preferably 1 to 20 and more preferably 1 to 10 is listed, such as methyl, ethyl, n-propyl, isopropyl, n-butyl, isobutyl, sec-butyl, tert-butyl, n-amyl, n-hexyl, and n-octyl. As the cycloalkyl, monocyclic, polycyclic or condensed-ring type cycloalkyl with a carbon number of 3 to 30, preferably 3 to 20 and more preferably 3 to 10 is listed, such as cyclopropyl, cyclopentyl, and cyclohexyl. As the aralkyl, groups obtained by substituting at least one hydrogen atom in the aforementioned alkyl with the aforementioned aryl are listed, such as aralkyl with a preferred carbon number of 7 to 15, specifically benzyl, 1-phenethyl, 2-phenethyl, 1-phenylpropyl, 3-naphthylpropyl, etc.

As a preferred technical solution of the present invention, as the aryl, monocycli, polycyclic or condensed-ring type aryl with a carbon number of 6 to 36, preferably 6 to 18 and more preferably 6 to 14 is listed, such as phenyl, naphthyl, anthryl and phenanthryl biphenyl. As aromatic heterocyclyl, penta or hexa monocyclic, polycyclic or condensed-ring type aromatic heterocyclyl with 2 to 15 carbon atoms is listed. These groups contain at least one, preferably 1 to 3 heteroatoms such as nitrogen atoms, oxygen atoms and/or sulfur atoms. For example, furyl, thienyl, pyridyl, pyrimidinyl, pyrazinyl, pyridazinyl, pyrazolyl, imidazolyl, oxazolyl, thiazolyl, benzofuryl, benzothiophenyl, quinolyl, isoquinolyl, quinoxalinyl, phenazinyl, quinazolinyl, naphthyridinyl, benzimidazolyl, benzoxazolyl, benzothiazolyl, acridinyl, etc.

As a preferred technical solution of the present invention, as the alkoxy, the alkoxy formed by linear or branched alkyl with a carbon number of 1 to 20, preferably 1 to 15 and more preferably 1 to 10 is listed, such as methoxy, ethoxy, n-propoxy, isopropoxy, n-butoxy, isobutoxy, sec-butoxy, tert-butoxy, and n-pentyloxy. As the cycloalkoxy, the cycloalkoxy formed by the polycyclic or condensed-ring type cycloalkyl with a carbon number of 3 to 20, preferably 3 to 15 and more preferably 3 to 10 is listed, such as cyclopropoxy, cyclopentyloxy and cyclohexyloxy. As the aralkoxy, groups obtained by substituting at least one hydrogen atom in the alkyl or the cycloalkyl in the aforementioned alkoxy with the aforementioned aryl are listed, for example, the aralkoxy with a preferably carbon number of 7 to 15, such as benzyloxy, 1-phenylethoxy, 2-phenyl ethoxy, 1-phenylpropoxy, 2-phenylpropoxy, 3-phenylpropoxy, 4-phenylbutoxy, 1-naphthylmethoxy and 2-naphthylmethoxy.

As a preferred technical solution of the present invention, as the aryloxy, the aryloxy formed by monocycli, polycyclic or condensed-ring type aryl with a carbon number of 6 to 36, preferably 6 to 18 and more preferably 6 to 14 is listed, such as phenoxy, tolyloxy, xylyloxy and naphthoxy.

As a preferred technical solution of the present invention, as substituent amino, groups obtained by substituting 2 hydrogen atoms of amino with the same or different aforementioned alkyl, cycloalkyl, aryl, aralkyl or heterocyclyl are listed, specifically dialkylamino such as N,N-diethylin and N,N-diisopropylamino, bicycloalkylamino such as N,N-dicyclohexylamino, diarylamino such as N,N-diphenylamino and N-naphthyl-N-phenylamino, and diarylalkylamino such as N,N-dibenzylamino. Besides, the alkyl, the cycloalkyl, the aryl, the aralkyl and the heterocyclyl of the above substituent amino further have substituent groups.

As a preferred technical solution of the present invention, as the substituent groups on the above alkyl, aryl, alkoxy, aryloxy and amino, the substituent groups are listed as the alkyl, the aryl, the alkoxy and the aryloxy which are listed when $R^1$ and $R^2$ are described, the amino, halogen atoms, silyl and any protected hydroxy.

As a preferred technical solution of the present invention, the halogen atoms as the substituent groups of $R^1$ and $R^2$ are listed as fluorine atoms, chlorine atoms, bromine atoms and iodine atoms.

As a preferred technical solution of the present invention, the silyl as the substituent groups of $R^1$ and $R^2$ is listed as groups obtained by substituting 3 hydrogen atoms in the silyl with the aforementioned alkyl and aryl. For example, trimethylsilyl, triethylsilyl, tert-butyl dimethyl silyl, tert-butyldiphenyl silyl, triphenylsilyl, etc.

As a preferred technical solution of the present invention, the any protected hydroxy as the substituent groups of $R^1$ and $R^2$ is listed as non-protected hydroxy, or hydroxy protected by protecting groups such as the trimethylsilyl, the triethylsilyl, the tert-butyldimethyl silyl, and the tert-butyldiphenyl silyl, or hydroxy protected by conventional hydroxy protecting groups, such as benzyl and methoxymethyl.

As a preferred technical solution of the present invention, an ammonium source shown in above formula (2) is described.

$$R^3COONH_4 \qquad (2)$$

Above formula (2) represents the carboxylic acid ammonium salt, and a required equivalent is 1 to 100 times the substrate (1). $R^3$ represents different substituent groups, including alkyl, cycloalkyl, aryl, aralkyl, alkoxy, cycloalkoxy, aryloxy, aralkoxy and heterocyclyl. In addition, the alkyl, the cycloalkyl, the aryl, the aralkyl, the alkoxy, the cycloalkoxy, the aryloxy, the aralkoxy and the heterocyclyl also have substituent groups.

As a preferred technical solution of the present invention, the alkyl and the aryl are listed as the alkyl and the aryl which are listed when $R^1$ and $R^2$ in aforementioned formula (1) are described, preferably methyl, ethyl, propyl, tert-butyl, trifluoromethyl, phenyl, etc.

As a preferred technical solution of the present invention, the acid HX used in the above formula is described. HX represents the protonic acid, and X is the halogen anions, the carboxylate anions, the sulfooxy anions, the sulfate radical, the hydrogen sulfate radical, the dihydrogen phosphate radical, the monohydrogen phosphate radical, the phosphite radical, the nitrate radical, etc. Preferably hydrochloric acid, hydrobromic acid, sulfuric acid, methanesulfonic acid and p-toluenesulfonic acid.

As a preferred technical solution of the present invention, formula (5) of the catalyst used in the reaction of the present invention is described.

$$RuX_2L \qquad (5)$$

In the formula, Ru is metallic ruthenium.

X in the formula is the complex anion which is the halogen anions, the carboxylate anions, the sulfooxy anions, the sulfate radical, the hydrogen sulfate radical, the dihydrogen phosphate radical, the monohydrogen phosphate radical, the phosphite radical, the nitrate radical, etc. in formula (2).

In the formula, L is the chiral diphosphine ligand, and a structure of L is as shown in formula (6).

(6)

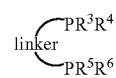

As a preferred technical solution of the present invention, in above formula (6), linker represents various chiral and achiral linking groups. $R^3$ to $R^6$ represent the identical or different substituent groups, including alkyl, cycloalkyl, aryl, aralkyl, alkoxy, cycloalkoxy, aryloxy, aralkoxy and heterocyclyl. Rings are formed between $R^3$ and $R^4$ and between $R^5$ and $R^6$. In addition, the alkyl, the cycloalkyl, the aryl, the aralkyl, the alkoxy, the cycloalkoxy, the aryloxy, the aralkoxy and the heterocyclyl also have substituent groups.

As a preferred technical solution of the present invention, the chiral and achiral linking groups, namely linker, are listed as center-chiral, axial-chiral, planar-chiral and helical-chiral linking groups containing carbon, preferably the chiral diphosphine ligand of the following structures.

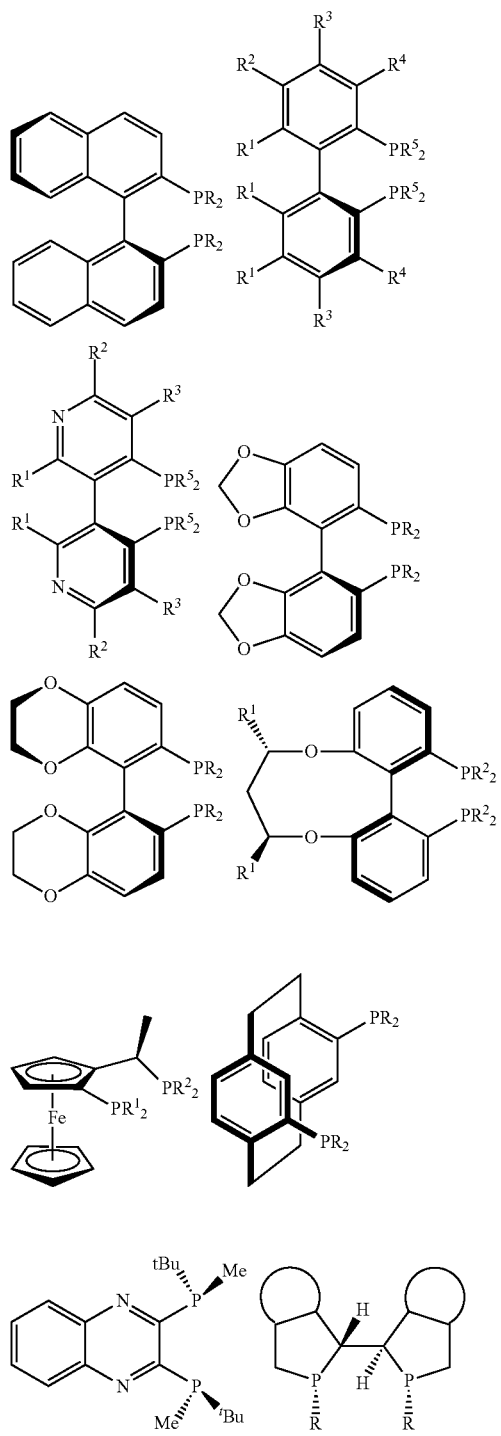

-continued

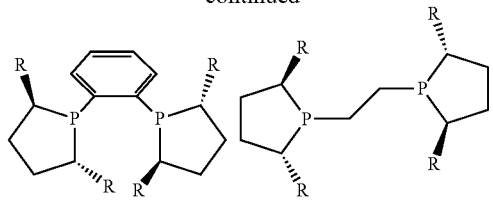

In the above structures, R and $R^1$ to $R^5$ are the groups represented by $R^1$ and $R^2$ in formula (1).

As a preferred technical solution of the present invention, the preparation method of the chiral amine of the present invention uses a single solvent or a mixed solvent. The solvent is specifically listed as alcohols such as methanol, ethanol, isopropanol, n-butanol, 2-butanol, tert-butanol, trifluoroethanol and hexafluoroisopropanol, aromatic hydrocarbon such as toluene and xylene, aliphatic hydrocarbon such as hexane and heptane, halohydrocarbon such as dichloromethane and chlorobenzene, and ethers such as ethyl ether, tetrahydrofuran, methyl tert-butyl ether and methyl cyclopentyl ether. The alcohols are specially and preferably trifluoroethanol and hexafluoroisopropanol. The use amount of the solvent is properly selected according to reaction conditions.

As a preferred technical solution of the present invention, pressure of the hydrogen used in the present invention is 10 to 200 atm, preferably 30 to 70 atm.

As a preferred technical solution of the present invention, the reaction temperature used in the present invention is 20° C. to 160° C., preferably 70° C. to 140° C.

As a preferred technical solution of the present invention, the use amount of the catalyst is determined based on a hydrogenation substrate, reaction conditions and a type of the catalyst, and a molar ratio of the catalyst to the substrate is in a range of 0.001 mol % to 10 mol %, preferably 0.01 mol % to 1 mol %.

As a preferred technical solution of the present invention, the reaction time is generally 0.5 to 240 h, preferably 16 to 32 h.

DETAILED DESCRIPTION OF THE PRESENT INVENTION

The present invention is described below through embodiments, but the present invention is not limited to the embodiments.

Embodiment 1

In an argon atmosphere, acetophenone (1 mmol, 120 mg), $RuX_2L$ and $NH_4X$ (2 mmol) were added into a 5 mL ampoule. A corresponding solvent (2 mL) was added, and a reaction flask was placed in an autoclave. Hydrogen was injected for replacement three times, wherein 10 atm of hydrogen was injected each time, and hydrogen of required pressure was injected the last time. The autoclave was placed in an oil bath which was preheated in advance to a corresponding temperature, and heating stirring was performed for 24 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain pure 1-phenylethylamine. For measurement of enantioselectivity of a product, the product needs to be acetylated first, and corresponding yields and enantioselectivity are as shown in Table 1.

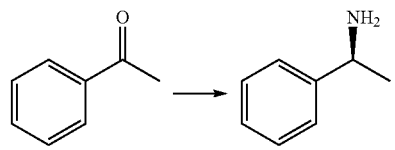

Compared with Entry 18 in embodiment 1, a 6 M hydrochloric acid solution was not added for heating treatment in post-treatment.

In an argon atmosphere, acetophenone (1 mmol, 120 mg), $Ru(OAc)_2L_1$ (0.1 mol %), $NH_4OAc$ (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and stirring was performed for 24 hours while heating was performed to 120° C. Cooling was performed to a room temperature. The hydrogen was slowly released, and the reaction flask was taken out. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was

TABLE 1

Preparation of Chiral 1-phenylethylamine through Asymmetric Reductive Amination of Acetophenone

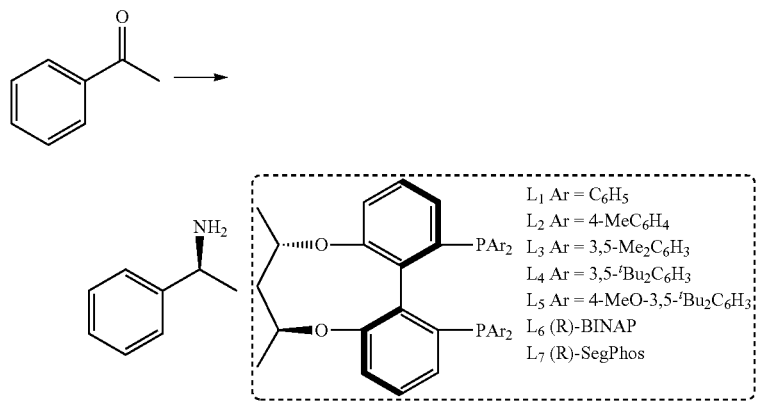

$L_1$ Ar = $C_6H_5$
$L_2$ Ar = 4-$MeC_6H_4$
$L_3$ Ar = 3,5-$Me_2C_6H_3$
$L_4$ Ar = 3,5-$^tBu_2C_6H_3$
$L_5$ Ar = 4-MeO-3,5-$^tBu_2C_6H_3$
$L_6$ (R)-BINAP
$L_7$ (R)-SegPhos

| Entry | $NH_4X$ | $RuX_2L$ (x mol %) | $H_2$ (atm) | Temp. (° C) | Solvent | Yield (%) | Ee (%) |
|---|---|---|---|---|---|---|---|
| 1 | $NH_4OAc$ | $Ru(OAc)_2L_1$ (1) | 50 | 80 | MeOH | 58 | 33 |
| 2 | $NH_4OAc$ | $Ru(OAc)_2L_1$ (1) | 50 | 80 | EtOH | 46 | 48 |
| 3 | $NH_4OAc$ | $Ru(OAc)_2L_1$ (1) | 50 | 80 | $^iPrOH$ | 35 | 59 |
| 4 | $NH_4OAc$ | $Ru(OAc)_2L_1$ (1) | 50 | 80 | THF | 18 | 57 |
| 5 | $NH_4OAc$ | $Ru(OAc)_2L_1$ (1) | 50 | 80 | TFE | 96 | 75 |
| 6 | $PhCOONH_4$ | $Ru(OAc)_2L_1$ (1) | 50 | 80 | TFE | 96 | 70 |
| 7 | $NH_4OAc$ | $RuCl_2L_1$ (1) | 50 | 80 | TFE | 91 | 78 |
| 8 | $NH_4OAc$ | $RuCl_2L_2$ (1) | 50 | 80 | TFE | 90 | 74 |
| 9 | $NH_4OAc$ | $RuCl_2L_3$ (1) | 50 | 80 | TFE | 89 | 76 |
| 10 | $NH_4OAc$ | $RuCl_2L_4$ (1) | 50 | 80 | TFE | 93 | 89 |
| 11 | $NH_4OAc$ | $RuCl_2L_5$ (1) | 50 | 80 | TFE | 94 | 94 |
| 12 | $NH_4OAc$ | $Ru(OAc)_2L_5$ (1) | 50 | 80 | TFE | 92 | 97 |
| 13 | $NH_4OAc$ | $Ru(OAc)_2L_5$ (1) | 70 | 80 | TFE | 98 | 96 |
| 14 | $NH_4OAc$ | $Ru(OAc)_2L_5$ (0.5) | 50 | 100 | TFE | 98 | 96 |
| 15 | $NH_4OAc$ | $Ru(OAc)_2L_6$ (1) | 50 | 80 | TFE | 92 | 65 |
| 16 | $NH_4OAc$ | $Ru(OAc)_2L_7$ (1) | 50 | 80 | TFE | 92 | 67 |
| 17 | $NH_4OAc$ | $Ru(OAc)_2L_5$ (0.1) | 60 | 120 | TFE | 80 | 94 |
| 18 | $NH_4OAc$ | $Ru(OAc)_2L_1$ (0.1) | 60 | 120 | TFE | 96 | 82 |
| 19 | $NH_4OAc$ | $Ru(OAc)_2L_1$ (0.01) | 60 | 120 | TFE | 38 | 82 | performed to obtain 97 mg of pure (S)-1-(phenyl)ethane-1-amine with 81% yield and 82% ee.

Embodiment 3

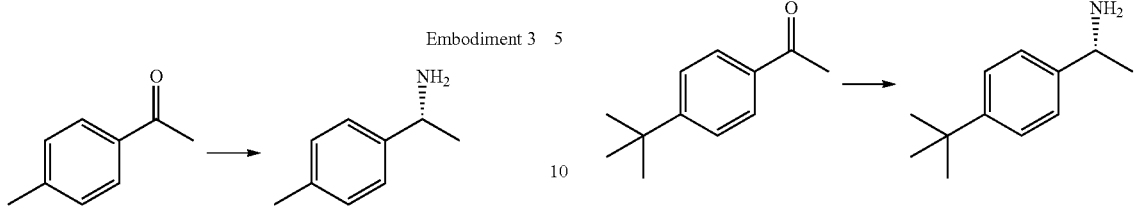

In an argon atmosphere, 4-methyl acetophenone (1 mmol, 134 mg), Ru(OAc)$_2$L$_5$ (0.5 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 117 mg of pure (R)-1-(p-methylphenyl)ethane-1-amine with 87% yield and 96% ee.

Embodiment 4

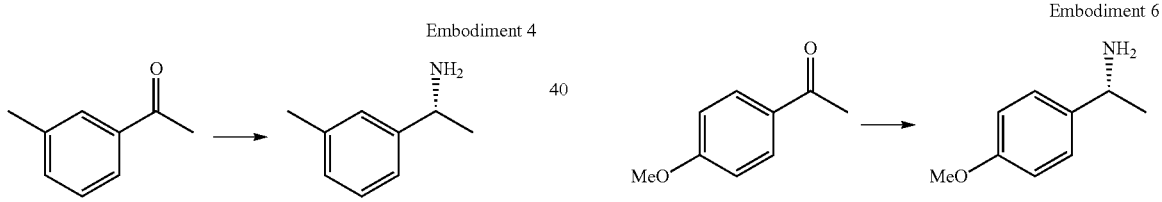

In an argon atmosphere, 3-methyl acetophenone (1 mmol, 134 mg), Ru(OAc)$_2$L$_5$ (0.5 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 120 mg of pure (R)-1-(m-methylphenyl)ethane-1-amine with 89% yield and 91% ee.

Embodiment 5

In an argon atmosphere, 4-tert-butyl acetophenone (1 mmol, 176 mg), Ru(OAc)$_2$L$_5$ (0.5 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 134 mg of pure (R)-1-(4-(tert-butyl)phenyl)ethane-1-amine with 76% yield and 87% ee.

Embodiment 6

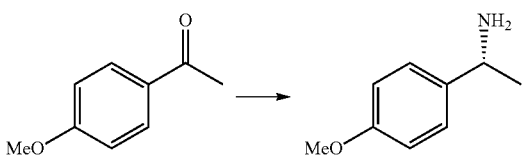

In an argon atmosphere, 4-methoxy acetophenone (1 mmol, 150 mg), Ru(OAc)$_2$L$_5$ (0.5 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 143.5 mg of pure (R)-1-(4-methoxyphenyl)ethane-1-amine with 95% yield and 89% ee.

Embodiment 7

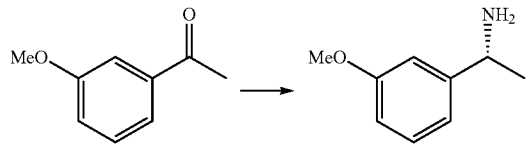

In an argon atmosphere, 3-methoxy acetophenone (1 mmol, 150 mg), Ru(OAc)$_2$L$_5$ (0.2 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 138 mg of pure (R)-1-(3-methoxyphenyl) ethane-1-amine with 91% yield and 94% ee.

Embodiment 8

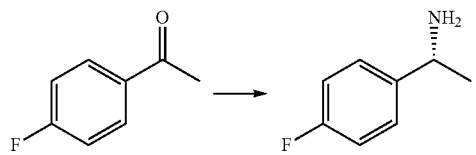

In an argon atmosphere, 4-fluoroacetophenone (1 mmol, 138 mg), Ru(OAc)$_2$L$_5$ (0.2 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 127 mg of pure (R)-1-(4-fluorophenyl) ethane-1-amine with 91% yield and 95% ee.

Embodiment 9

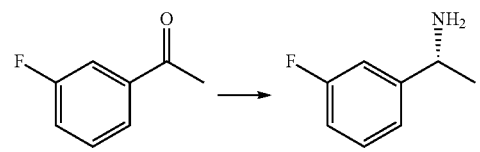

In an argon atmosphere, 3-fluoroacetophenone (1 mmol, 138 mg), Ru(OAc)$_2$L$_5$ (0.2 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 127 mg of pure (R)-1-(3-fluorophenyl) ethane-1-amine with 91% yield and 95% ee.

Embodiment 10

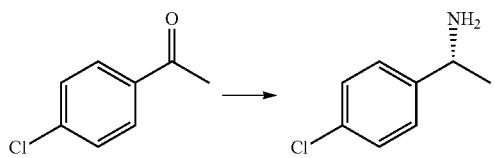

In an argon atmosphere, 4-chloroacetophenone (1 mmol, 154 mg), Ru(OAc)$_2$L$_5$ (0.5 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 120 mg of pure (R)-1-(4-chlorophenyl) ethane-1-amine with 77% yield and 96% ee.

Embodiment 11

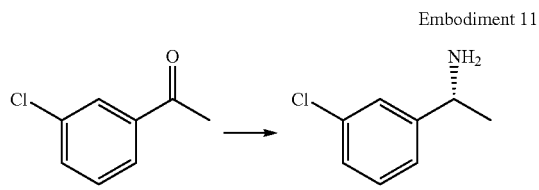

In an argon atmosphere, 3-chloroacetophenone (1 mmol, 154 mg), Ru(OAc)$_2$L$_5$ (0.5 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 121 mg of pure (R)-1-(3-chlorophenyl) ethane-1-amine with 81% yield and 94% ee.

Embodiment 12

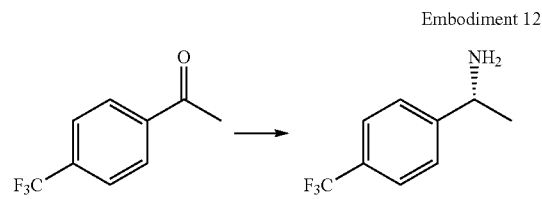

In an argon atmosphere, 4-trifluoromethyl acetophenone (1 mmol, 188 mg), Ru(OAc)$_2$L$_5$ (0.5 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 198 mg of pure (R)-1-(4-(trifluoromethyl) phenyl)ethane-1-amine with 75% yield and 96% ee.

Embodiment 13

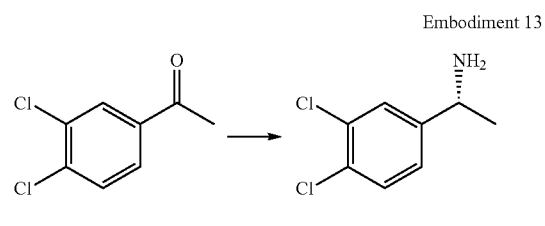

In an argon atmosphere, 3,4-dichloroacetophenone (1 mmol, 189 mg), Ru(OAc)$_2$L$_5$ (0.5 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 115 mg of pure (R)-1-(3,4-dichlorophenyl) ethane-1-amine with 89% yield and 90% ee.

Embodiment 14

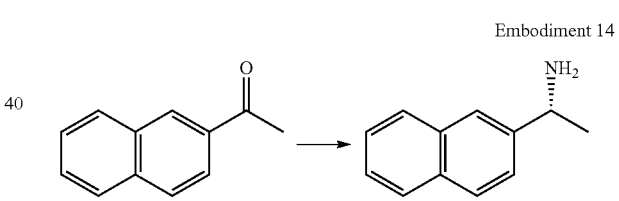

In an argon atmosphere, 2-acetonaphthone (1 mmol, 170 mg), Ru(OAc)$_2$L$_5$ (0.5 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 148 mg of pure (R)-1-(naphthalen-2-yl) ethane-1-amine with 89% yield and 94% ee.

Embodiment 15

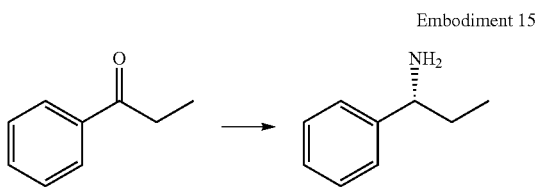

In an argon atmosphere, 1-propiophenone (1 mmol, 134 mg), Ru(OAc)$_2$L$_5$ (0.5 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 109 mg of pure (R)-1-phenylpropane-1-amine with 84% yield and 97% ee.

Embodiment 16

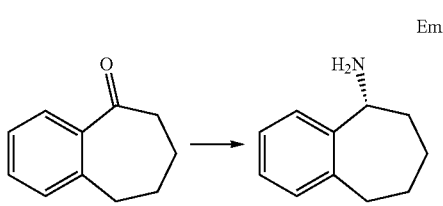

In an argon atmosphere, 6,7,8,9-tetrahydro-5H-benzo[7]cyclopentane-5-one (1 mmol, 160 mg), Ru(OAc)$_2$L$_1$ (0.5 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain pure (R)-6,7,8,9-tetrahydro-5H-benzo[7]cyclopentane-5-amine with 91% yield and 84% ee.

Embodiment 17

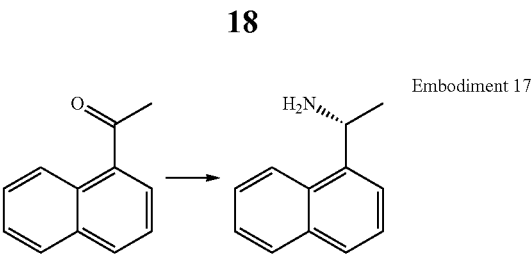

In an argon atmosphere, 1-acetonaphthone (5 mmol, 850 mg), Ru(OAc)$_2$L$_1$ (0.1 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 774 mg of pure (R)-1-(naphthalen-1-yl)ethane-1-amine with 89% yield and 97% ee.

Embodiment 18

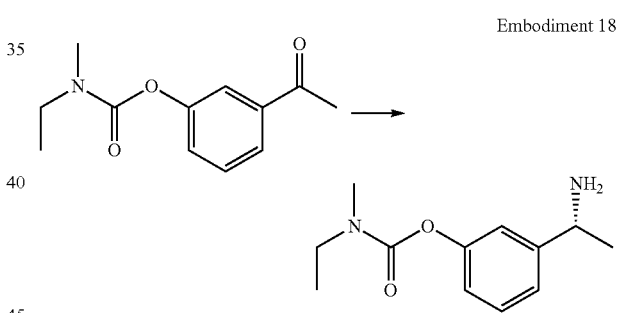

In an argon atmosphere, 3-acetylphenylethyl(methyl)carbamate (1 mmol, 221 mg), Ru(OAc)$_2$L$_1$ (0.2 mol %), NH$_4$OAc (2 mmol, 154 mg) and trifluoroethanol (2 mL) were added into a 5 mL ampoule. A reaction flask was placed in an autoclave. Hydrogen was injected for replacement three times, wherein 10 atm of hydrogen was injected each time, and 50 atm of hydrogen was injected the last time. The autoclave was placed in an oil bath which was preheated in advance to a corresponding temperature, and heating stirring was performed for 20 hours. Cooling was performed to a room temperature. The hydrogen was slowly released, and the reaction flask was taken out. 3 mL of a 6 M hydrogen chloride solution was added, and heating was performed at 80° C. for 6 hours. Cooling was performed, and washing was performed with ethyl ether two times. A 4 M sodium hydroxide solution was used for neutralization till pH was 10. Extraction was performed with ethyl ether three times, and organic phases were combined. Anhydrous sodium sulfate was used for drying, and vacuum drying was performed to obtain 186 mg of pure (R)-3-(1-aminoethyl)phenylethyl(methyl)carbamate with 84% yield and 94% ee.

The above embodiments are preferred implementations of the present invention, but the implementations of the present invention are not limited by the above embodiments. Any other change, modification, substitution, combination and simplification without departing from the spiritual essence and principle of the present invention shall be equivalent replacement modes, which are contained in the protection scope of the present invention.

What is claimed is:

1. A method for preparing a chiral primary amine, comprising:
    in an argon atmosphere, adding a ketone compound, a ammonium salt, a ruthenium-diphosphine catalyst and an organic solvent to a reaction flask;
    placing the reaction flask into an autoclave, followed by hydrogen injection, wherein a pressure of the hydrogen is 10-200 atm;
    performing an oil-bath stirring treatment on the autoclave at 20-160° C. for 0.5-240 h to generate an intermediate;
    cooling the autoclave to a room temperature and releasing the hydrogen;
    adding a protonic acid into the reaction flask for reaction at 80° C. for 6.0 h to obtain a reaction mixture; and
    subjecting the reaction mixture to neutralizing, washing, extracting and drying to obtain the chiral primary amine.

2. The method of claim 1, wherein the ketone compound is one of 4-methyl acetophenone, 3-methyl acetophenone, 4-tert-butyl acetophenone, 4-chloroacetophenone, 3-chloroacetophenone, 4-trifluoromethyl acetophenone, 3,4-dichloroacetophenone, 2-acetonaphthone, 1-propiophenone, 6,7,8,9-tetrahydro-5H-benzo[7]cyclopentane-5-one, 1-acetonaphthone and 3-acetylphenylethyl(methyl)carbamate.

3. The method of claim 1, wherein the ammonium salt is an ammonium carboxylate salt.

4. The method of claim 3, wherein a general formula of the ammonium carboxylate salt is $R^3COONH_4$, wherein $R^3$ is one of alkyl, cycloalkyl, aryl, aralkyl, alkoxy, cycloalkoxy, aryloxy, aralkoxy and heterocyclyl.

5. The method of claim 1, wherein a general formula of the ruthenium-diphosphine catalyst is $RuX_2L$; wherein X is one of halogen anions, carboxylate anions, sulfooxy anions, a sulfate radical, a hydrogen sulfate radical, a dihydrogen phosphate radical, a monohydrogen phosphate radical, a phosphite radical, and a nitrate radical; and L is a chiral diphosphine ligand.

6. The method of claim 1, wherein the protonic acid is one of hydrochloric acid, hydrobromic acid, sulfuric acid, methanesulfonic acid and p-toluenesulfonic acid.

* * * * *